United States Patent [19]

Goldwasser et al.

[11] Patent Number: 4,740,579

[45] Date of Patent: Apr. 26, 1988

[54] SYNTHESIS OF DIHYDROXY-TERMINATED POLY(2,2,3,3,4,4-HEXAFLUOROPENTANE-1,5-DIOL FORMAL)

[75] Inventors: Judah M. Goldwasser; Horst G. Adolph, both of Silver Spring, Md.

[73] Assignee: The United States of America as represented by the Secretary of the Navy, Washington, D.C.

[21] Appl. No.: 52,503

[22] Filed: May 5, 1987

[51] Int. Cl.$^4$ .................. C08G 10/02; C08G 73/24
[52] U.S. Cl. .................. 528/242; 528/244; 528/401
[58] Field of Search .......... 528/242, 244, 401

[56] References Cited

U.S. PATENT DOCUMENTS 3,419,531 12/1968 Trischler .................. 528/244 X
3,442,865 5/1969 Weissermel et al. ............ 528/244

Primary Examiner—Lucille M. Phynes
Attorney, Agent, or Firm—Kenneth E. Walden; Roger D. Johnson

[57] ABSTRACT

A method of producing dihydroxy-terminated poly(2,2,3,3,4,4-hexafluoropentane-1,5-diol formal) of a desired number average molecular weight by controlling the relative amounts of 1,3-dioxa-5,5,6,6,7,7-hexafluorocyclooctane monomer, 2,2,3,3,4,4-hexafluoropentane-1,5-diol, and the catalyst trifluoromethane sulfonic acid (having a determined activity) used to produce the polymer.

7 Claims, No Drawings

SYNTHESIS OF DIHYDROXY-TERMINATED POLY(2,2,3,3,4,4-HEXAFLUOROPENTANE-1,5-DIOL FORMAL)

BACKGROUND OF THE INVENTION

This invention relates to fluoropolymers and more particularly to dihydroxy-terminated poly(2,2,3,3,4,4-hexafluoropentane-1,5-diol formal).

The copolymerization of diols with formaldehyde has in the past been accomplished by a number of means. Originally, the most common method employed was acid transformylation of the diol with a dialkyl formal. Usually, the acid catalyst was p-toluenesulfonic acid (see J. W. Hill and W. H. Carother Amer. Chem. Soc., 57, 925 (1935); F. D. Trischler and J. Hollander, J Polym. Sci. A-1, 5, 2343 (1967)). This procedure, however, required high temperatures and constant removal of the alcohol byproduct in order to drive the reaction forward to good yield.

Subsequently, formation of polyformals has been achieved by reaction of the diol with formaldehyde either in the form of paraformaldehyde or in the form of trioxane. The procedures also called for reactions to take place at high temperatures, in a water immiscible solvent, and in the presence of an acid catalyst. Water byproduct formed during the polycondensation process was also required to be removed by azeotropic distillation in order to drive the reaction forward to good yield. (See W. J. Jackson, Jr., and J. R. Caldwell, ACS Adv. Chem Ser. 34, 200 (1982); F. D. Trischler and J. Hollander, J. Polym. Sci. A-1, 5, 2343 (1967)).

Alternatively, synthesis of polyformals has been carried out by acid catalyzed ring opening polymerization of the preformed cyclic formal. This method, by its nature, obviates the need for high temperature reactions and continuous removal of condensation products since none exist. (See J. Furukawa and K. Tada in "Kinetics and Mechanisms of Polymerization", Vol. 2, K Frisch & S. Reegen eds., M. Dekker, New York, 1969, pg. 159ff.)

The object polyformal has been previously synthesized using all three of the aforementioned methods. (see F. D. Trischler and J. Hollander, J. Polym. Sci. A-1, 5, 2343 (1967); P. Johncock, Brit. Pat. No. 1294657.) However, all of these procedures suffer from deficiencies which the present invention was designed to overcome. The transformylation procedure requires high temperatures and facility for continuous removal of the alcohol product. There is no molecular weight control, the yields obtained were abysmally low, and the polymer terminal groups were nonfunctional hydrocarbon. The condensation procedure using trioxane also requires high temperature reactions and continuous removal of the condensation byproduct. There is also no molecular weight control with this procedure. In fact, polymers produced using this procedure are merely oligomeric, and are not suitable for curing in many applications. As well, the ultimate conversion (yield) attained for this procedure is well below those obtained using the procedure of the present invention.

The ring opening polymerization technique employed previously to produce the object polyformal overcame the deficiencies presented by the condensation techniques but nonetheless presented others which the present invention was designed to overcome. First, no molecular weight control over the resultant polymer was exercised. Second, sophisticated high vacuum techniques had to be employed in order to introduce small amounts of $PF_5$ catalyst. In cases where metallic Lewis acid catalysts were employed, high purity solvents free of nucleophilic contaminants had to be prepared for the introduction of precise amounts of catalyst solution. In addition, no precautions were taken to ensure that hydroxyl bifunctionality was retained.

SUMMARY OF THE INVENTION

Accordingly, an object of this invention is to provide a new method of preparing dihydroxy-terminated poly(2,2,3,3,4,4-hexafluoropentane-1,5-diol formal).

Another object of this invention is to provide a method of producing dihydroxy-terminated poly(2,2,3,3,4,4-hexafluoropentane-1,5-diol formal) with close control over the number average molecular weight ($\overline{M}_n$).

A further object of this invention is to provide a method of producing dihydroxy-terminated poly(2,2,3,3,4,4 -hexafluoropentane-1,5-diol formal) such that the polymer is functionally terminated on both ends with hydroxy groups.

Yet another object of this invention is to provide a method of producing dihydroxy-terminated poly(2,2,3,3,4,4-hexafluoropentane-1,5-diol formal) in high yield.

A still further object of this invention is to provide an economical method of producing dihydroxy-terminated poly(2,2,3,3,4,4-hexafluoropentane-1-5-diol formal).

These and other objects of this invention are accomplished by providing a method of producing dihydroxy-terminated poly(2,2,3,3,4,4-hexafluoropentane-1,5-diol formal) of a desired number average molecular weight by controlling the relative amounts of 1,3-dioxa-5,5,6,6,7,7-hexafluorocyclooctane monomer, 2,2,3,3,4,4-hexafluoropentane-1,5-diol, and the catalyst trifluoromethane sulfonic acid (having a determined activity) used to produce the polymer.

DETAILED DESCRIPTION OF THE PREFERRED EMBODIMENT

The process of this invention provides means for producing dihydroxy-terminated poly(2,2,3,3,4,4-hexafluoropentane-1,5-diol formal) of a selected number-average molecular weight, $\overline{M}_n$. Trifluoromethane sulfonic (triflic) acid, $CF_3SO_3H$, is used to catalyze the cationic ring opening polymerization of 1,3-dioxa-5,5,6,6,7,7-hexafluorocyclooctane into dihydroxy-terminated poly(2,2,3,3,4,4-hexafluoropentane-1,5-diol formal). The initiation step may be represented as

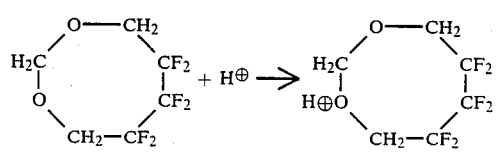

Propagation may be represented as

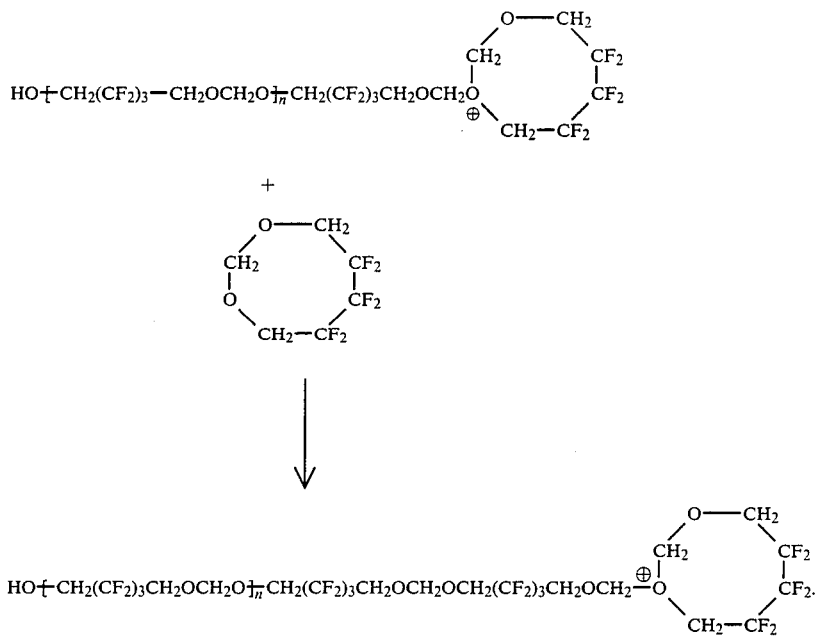

The number-average molecular weight, $\overline{M}_n$, of the dihydroxy-terminated poly(2,2,3,3,4,4-hexafluoropentane-1,5-diol formal) decreases as the number of polymer chains initiated is increased for a given quantity of 1,3-dioxa-5,5,6,6,7,7-hexafluorocylooctane monomer ($n_{monomer}$). The number of polymer chains initiated is directly proportional to the product of the number of moles of trifluoromethane sulfonic acid ($n_{acid}$) and the activity of the acid (A). Thus, as $(n_{acid} \times A)/n_{monomer}$ is decreased, the number-average molecular weight ($\overline{M}_n$) of the polymer produced will increase. However, the time required for completion of the reaction also increases and sets practical limits on how low ($n_{acid} \times A)/n_{monomer}$ should be and thus what the number average molecular weight can be. In Example 2, dihydroxy-terminated poly(2,2,3,3,4,4-hexafluoropentane-1,5-diol formal) having a measured number average molecular weight of 21,000 was obtained in a 62 percent yield by using trifluoromethane sulfonic acid with an active acid strength of $(n_{acid} \times A)/n_{monomer} =$ $(0.452 \text{ mmole})(0.18)/(7.63 \text{ mmole}) = 1.066 \times 10^{-2}$.

Dihydroxyterminated poly(2,2,3,3,4,4-hexafluoropentane-1,5-diol formal) polymers of lower number-average molecular weights (i.e., lower than 21,000) are useful as prepolymers for polymer formulations. For instance, these polymers in the number-average molecular weight range of about 2,000 to about 4,000 are useful as prepolymers in stable energetic explosive and propellant formulations.

By increasing the active acid strength of the trifluoromethane sulfonic acid catalyst $(n_{acid} \times A)/n_{monomer}$, the $\overline{M}_n$ of the dihydroxy-terminated poly(2,2,3,3,4,4,-hexafluoropentane-1,5-diol formal) and the reaction time can both be reduced. However, several practical considerations limit how far this approach can be carried. First, trifluoromethane sulfonic acid is expensive and would have to be recovered from the reaction mixture. Second, higher concentrations of the acid catalyst increase side reactions, resulting in lower yields and lower purity of products. [Note, it is impractical to adjust the activity, A, of trifluoromethane sulfonic acid; therefore, the active acid strength of the acid catalyst, $(n_{acid} \times A)/n_{monomer}$, is adjusted by changing the molar ratio of acid to monomer $(n_{acid}/n_{monomer})$.]

In the present process the strength of trifluoromethane sulfonic acid, $(n_{acid} \times A)/n_{monomer}$, used is selected to provide a reasonable reaction time with a minimum of side reaction. Ranges of $(n_{acid} \times A)/n_{monomer}$ are from 0.0050 to 0.0350, preferably from 0.0075 to 0.0250, and more preferably from 0.0100 to 0.0150. Note that like the activity (A), $(n_{acid} \times A)/n_{monomer}$ is a dimensionless number.

In order to achieve a lower number average molecular weight dihydroxy-terminated poly(2,2,3,3,4,4-hexafluoropentane-1,5-diol formal) polymer or prepolymer, a precise amount of 2,2,3,3,4,4-hexafluoropentane-1,5-diol is added to the 1,3-dioxa-5,5,6,6,7,7-hexafluorocyclooctane monomer prior to the addition of the acid catalyst. The 2,2,3,3,4,4-hexafluoropentane-1,5-diol functions as a chain transfer agent by regenerating a hydrogen ion H+ as it adds on to a polymer chain and terminates it:

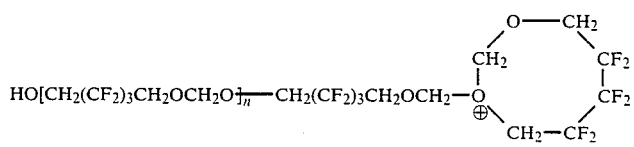

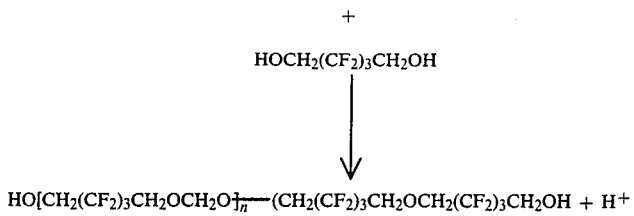

$$HO[CH_2(CF_2)_3CH_2OCH_2O]_n\!-\!\!-\!(CH_2(CF_2)_3CH_2OCH_2(CF_2)_3CH_2OH + H^+$$

Number-average molecular weight control is achieved by dissolving predetermined amounts 2,2,3,3,4,-hexafluoropentane-1,5-diol in predetermined amounts of the 1,3-dioxa-5,5,6,6,7,7-hexafluorocyclooctane monomer before a predetermined amount of trifluoromethane sulfonic acid catalyst is added. The relative amounts of these ingredients are formulated according to the formula $$\overline{M}_n = \frac{(n_{monomer})(M_{monomer})}{(n_{acid})(A) + n_{diol}} + \frac{(n_{diol})(M_{diol})}{(n_{acid})(A) + n_{diol}}$$

wherein (1) $\overline{M}_n$ is the target number-average molecular weight (2) A = is the activity of the trifluoromethane sulfonic acid batch, (3) $n_{monomer}$=the number of moles of 1,3-dioxa-5,5,6,6,7,7-hexafluorocyclooctane used, (4) $n_{acid}$=moles of trifluoromethane sulfonic acid selected to provide an acid catalyst strength $(n_{acid})$-$(A)/n_{monomer}$ in the desired range, (5) $n_{diol}$ is the number of moles of the 2,2,3,3,4,4-hexafluoropentane-1,5-diol to be used as calculated from the equation, (6) $M_{monomer}$ is the molecular weight ($\approx$224) of 1,3-dioxa-5,5,6,6,7,7-hexafluorocyclootcane and $M_{diol}$ is the molecular weight ($\approx$212) of 2,2,3,3,4,4-hexafluoropentane-1,5-diol. Note that the strength of the acid used $(n_{acid})(A)/n_{monomer}$ sets the upper limit on the number-average molecular weight of the polymer and that the diol is added to reduce the number-average molecular weight to a desired value below this maximum.

Trifluoromethane sulfonic acid is extremely reactive and may decrease in activity with age or in the presence of minor impurities. Therefore the activity of each batch of the trifluoromethane being used must be determined.

The activity of the batch of trifluoromethane sulfonic acid to be used is determined by the ring-opening polymerization of $n_{monomer}$ moles of the dried 1,3-dioxa-5,5,6,6,7,7-hexafluorocyclooctane monomer (M.W. 224) in the presence of $n_{acid}$ moles of the trifluoromethane sulfonic acid as catalyst. The activity of a given batch of acid does not vary significantly with temperature, particularly over the range of 50° C. to 70° C. The activity (A) of the trifluoromethane sulfonic acid is $$A = \frac{\overline{M}_{calc}}{\overline{M}_{obt}}$$

where $\overline{M}_{obt}$ is the number average molecular weight observed or determined for the actual product produced by the reaction. $\overline{M}_{obt}$ may be determined by any conventional method such as gel permeation chromatography. $\overline{M}_{calc}$ is calculated from the following formula $$\overline{M}_{calc} = \frac{(n_{monomer})(M_{monomer})}{n_{acid}}.$$

wherein $n_{monomer}$ is the number of moles of 1,3-dioxa-5,5,6,6,7,7-hexafluorocyclooctane monomer, and $n_{acid}$ is the number of moles of trifluoromethane sulfonic acid used in the reaction. The molecular weight of 1,3-dioxa-5,5,6,6,7,7-hexafluorocyclooctane ($M_{monomer}$) is 224.

Note that it is critical that both the 1,3-dioxa5,5,6,6,7,7-hexafluorocyclooctane monomer and the polyfluorinated diol be dry and free of water. Water will lower the activity of the trifluoromethane sulfonic acid and interfere with the polymerization of the monomer.

The 2,2,3,3,4,4-hexafluoropentane-1,5-diol is dissolved in the 1,3,dioxa-5,5,6,6,7,7-hexafluorocyclooctane monomer prior to the addition of the trifluoromethane sulfonic acid catalyst. The acid catalyst is added in a way which avoids locally high concentrations of the acid. In examples 2 through 5, the trifluoromethane sulfonic acid catalyst was added slowly with continuous stirring of the diol/monomer reaction mixture. The stirring was continued after addition of the catalyst until reaction was completed. Conventional methods of adding polymerized catalysts should be used to prevent high local concentration of the catalyst in industrial scale processing.

The reaction temperature is not an important factor in determining the molecular weight of the product polymers and prepolymers. However, because of the limited solubility of 2,2,3,3,4,4-hexafluoropentane-1,5-diol in the 1,3-dioxa5,5,6,6,7,7-hexafluorocyclooctane monomer at low temperatures, the lower reaction temperature limit is preferably 50° C., more preferably 55° C. and most preferably about 60° C. A temperature of 55° C. will provide sufficient solubility for most applications ana a temperature of at least 60° C. will provide sufficient solubility for the entire polymer or prepolymer number average weight range. The reaction temperature is limited at the upper end of the range by practical considerations such as the volatilities or boiling points of the reactants. In general little is to be gained by running the reaction at a temperature above 70° C. A preferred upper limit is 65° C. with about 60° C. being most preferred.

Upon completion of the reaction, the product is washed with a mixture of aqueous hydrogen peroxide, strong base ( 10% NaOH, KOH, etc.), and brine (NaCl or KCl). This procedure destroys and removes the trifluoromethane sulfonic acid catalyst. In addition, the active polymer end groups which did not react with the 2,2,3,3,4,4-hexafluoropentane-1,5-diol react with water to form formal end groups which are then deformylated by peroxide (e.g., $H_2O_2$) and base to form a hydroxy end group:

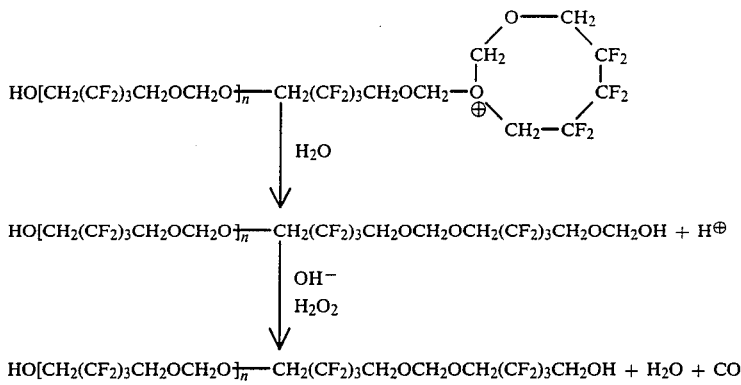

HO[CH$_2$(CF$_2$)$_3$CH$_2$OCH$_2$O]$_{\overline{n}}$—CH$_2$(CF$_2$)$_3$CH$_2$OCH$_2$OCH$_2$(CF$_2$)$_3$CH$_2$OCH$_2$OH + H$^{\oplus}$

↓ OH$^-$
   H$_2$O$_2$

HO[CH$_2$(CF$_2$)$_3$CH$_2$OCH$_2$O]$_{\overline{n}}$—CH$_2$(CF$_2$)$_3$CH$_2$OCH$_2$OCH$_2$(CF$_2$)$_3$CH$_2$OH + H$_2$O + CO$_2$.

As illustrated by examples 3, 4, and 5, this process works well in producing dihydroxy-terminated poly(2,2,3,3,4,4-hexafluoropentane-1,5-diol formal) polymers and prepolymers of desired molecular weights. The measured number-average molecular weights in these examples were only off by about 5 to 10 percent from the calculated or predicted number-average molecular weights. Moreover, the dispersities ($\overline{M}_w/\overline{M}_n$) for examples 3, 4, and 5 were 2.2, 1.98, and 2.14 respectively.

The general nature of the invention having been set forth, the following examples are presented as specific illustrations thereof. It will be understood that the invention is not limited to these specific examples but is susceptible to various modifications that will be recognized by one of ordinary skill in the art.

Example 1 illustrates a method for preparing the cyclic monomer starting material.

EXAMPLE 1

(Prior Art)

1,3-dioxa-5,5,6,6,7,7-hexafluorocyclooctane 318.13 g of 2,2,3,3,4,4-hexafluoropentane-1,5-diol (1.50 mol) and 48.29 g of paraformaldehyde (1.61 mol) were placed in a 3L 3-neck flask fitted with a thermometer and mechanical stirrer. 1200 mL of dichloromethane were added, and the slurry was stirred vigorously. The internal temperature was 20° C. 127.4 mL (216.1 g, 1.44 mol) of trifluoromethane sulfonic acid was added rapidly; the temperature dropped to 18° C., then rose to 23° C., then slowly dropped again. After 2 hours stirring 800 mL of ice-water were added, the mixture was stirred 30 min., and the layers were separated. The aqueous layer was washed with 200 mL of dichloromethane, and the combined dichloromethane layers were washed with 2×500 mL of 5% KOH solution. After drying (MgSO$_4$) and filtering, the dichloromethane was distilled off at atmospheric pressure to a bath temperature of 150° C., using a Vigreux column to facilitate separation from the product. The crude product was transferred to a smaller round bottom flask and was vacuum distilled through a Vigreux column into an ice-cooled receiver; b.p. 65° C. at ≈12 Torr. A forerun of about 50 g was collected which contained about 2% of trioxane by NMR. The main fraction weighed 239.5 g. About 5 g of material was distilled from the forerun through a Vigreux column in vacuo; this contained most of the trioxane. The pot residue was combined with the main fraction to give 284.5 g (84.6%) of pure product; m.p. 24–25° C.; density=1.584 g/cm$^3$.

The original aqueous phase was extracted with ether; the KOH solution was acidified and also extracted with ether. Work-up gave 16.5 g of recovered diol. The pot residue from the vacuum distillation (polymeric material) weighed 10.7 g; 0.7 g was recovered from a dry-ice trap which was used in the distillation. The total amount of recovered material, including the trioxane rich fraction, was 32.9 g, corresponding to about 10% of the diol used.

Example 2 illustrates a method for determining the activity of the trifluoromethane sulfonic acid.

EXAMPLE 2

Dihydroxy-terminated Poly(2,2,3,3,4,4-hexafluoropentane-1,5-diol formal)

To 1.71 g (7.63 mmole) of previously distilled and dried (sieves) 1,3-dioxa-5,5,6,6,7,7-hexafluorocyclooctane were added 40μL (0.452 mmole) trifluoromethane sulfonic acid with stirring at room temperature (22° C.). The reaction mixture was allowed to stand at room temperature for 4 hours in the stoppered reaction vessel. The viscous polymer was then dissolved in 3 ml of CH$_2$Cl$_2$ which were added to the reaction mixture. The trifluoromethane sulfonic acid was neutralized with triethyl amine. Volatiles were pumped off under high vacuum at 115° for 12 hours. Recovered polymer weighed 1.06 g (62%). Number average molecular weight ($\overline{M}_n$) was measured to be 21000. Weight average molecular weight($\overline{M}_w$) was measured to be 25600. $\overline{M}_w/\overline{M}_n$=1.2. (Molecular weight measurements were made by gel permeation chromatograph (GPC).) Calculated $\overline{M}_n$=3781. Trifluoromethane sulfonic acid activity (A) was 0.18.

EXAMPLE 3

Dihydroxy-terminated Poly(2,2,3,3,4,4-hexafluoropentane-1,5-diol formal)

200 mg (0.943 mmole) of 2,2,3,3,4,4-hexafluoropentane-1,5-diol (dried) were dissolved into 2.80 g (12.50 mmole) of distilled and dried (sieves) 1,3-dioxa-5,5,6,6,7,7-hexafluorocyclooctane at 60° C. To this solution, 80μL (0.904 mmole) trifluoromethane sulfonic acid were added with stirring. The reaction mixture was allowed to stand in a stoppered flask at 60° C. for 36 hours at which time 30 ml of dichloroethane were then added to dissolve the mixture. The solution was washed twice with 5 ml of 30% H$_2$O$_2$+20 ml of 10% aqueous NaOH +25 ml of brine and twice with brine. The dichloroethane solution was filtered through Whatman 1PS filter paper and the bulk of the solvent removed by rotary evaporation. The residue was subjected to high vacuum at 150° C. for several hours to remove unreacted monomer. Recovered polymer weighed 2.2 g (74%). $\overline{M}_n=3000$, $\overline{M}_w=6800$, $\overline{M}_w/\overline{M}_n=2.2$. $\overline{M}_n$ (calculated) =2713.

EXAMPLE 4

Dihydroxy-terminated Poly(2,2,3,3,4,4-hexafluoropentane-1,5-diol formal)

750 mg (3.538 mmole) of 2,2,3,3,4,4-hexafluoropentane-1,5-diol, (dried) were dissolved into 7.90 g (35.27 mmole) of distilled, dried (sieves) 1,3-dioxa-5,5,6,6,7,7-hexafluorocyclooctane at 60° C. To this solution were added 75μL (0.848 mmole) trifluoromethane sulfonic acid while stirring. The stoppered reaction mixture was allowed to stand at 60° C. for 24 hours. Molecular weight measurements were then performed on the crude material excluding unreacted monomer. $\overline{M}_n$ =2200, $\overline{M}_w$ =4400, $\overline{M}_w/\overline{M}_n$ =1.98. $\overline{M}_n$ (calculated) =2340.

EXAMPLE 5

Dihydroxy-terminated Poly(2,2,3,3,4,4-hexafluoropentane-1,5-diol formal)

2.8 g (13.21 mmole of 2,2,3,3,4,4,-hexafluoropentane-1,5-diol (dried) were dissolved into 39.9 g (176.79 mmole) of 1,3-dioxa-5,5,6,6,7,7-hexafluorocyclooctane at 60° C. While stirring 1.0 ml (11.307 mmole) of trifluoromethane sulfonic acid was added in 100μL increments over the period of 1 hour. The stoppered reaction mixture was then allowed to stand at 60° C. for 24 hours, after which time 250 ml dichloroethane were added to dissolve the mass. The solution was then washed twice with 10 ml of 30% H$_2$O$_2$ +115 ml if 10% aqueous NaOH +125 ml of brine and twice with brine. The dichloroethane solution was then passed through Whatman IPS filter paper and most of the solvent was removed by rotary evaporation. The residue was subjected to high vacuum at 140° C. for several hours. Recovered polymer weighed 26.95 g (72.5%), $\overline{M}_n=3100$, $\overline{M}_w=7000$, $\overline{M}_w/\overline{M}_n=2.14$ by GPC. $\overline{M}_n$ (calculated) =2800. Equivalent weight (g of polymer per OH group) was measured by a nuclear magnetic resonance spectrometric technique to be 1537. Therefore, the hydroxyl functionality (f) is 2.02.

Obviously, numerous modification and variations of the present invention are possible in light of the above teachings. It is therefore to be understood that within the scope of the appended claims the invention may be practiced otherwise than as specifically described herein.

We claim:

1. A process for producing a dihydroxy-terminated poly(2,2,3,3,4,4-hexafluoropentane-1,5-diol formal) of a target numerical number-average molecular weight $\overline{M}_n$, comprising:
   a. Selecting $n_{acid}$ moles of trifluoromethane sulfonic acid having an activity of A as a catalyst;
   b. forming a reaction mixture of $n_{monomer}$ moles of 1,3-dioxa-5,5,6,6,7,7-hexafluorocyclooctane monomer and $n_{diol}$ moles of 2,2,3,3,4,4,-hexafluoropentane-1,5-diol wherein $n_{diol}$ is calculated from the formula $$\overline{M}_n = \frac{(n_{monomer})(M_{monomer})}{(n_{acid})(A) + n_{diol}} + \frac{(n_{diol})(M_{diol})}{(n_{acid})(A) + n_{diol}}$$

wherein $M_{monomer}$ is the molecular weight of 1,3-dioxa-5,5,6,6,7,7-hexafluorocyclooctane, $M_{diol}$ is the molecular weight of 2,2,3,3,4,4-hexafluoropentane-1,5-diol, and wherein $\overline{M}_n$, $n_{monomer}$, $n_{acid}$, and A are as defined above;

c. dispersing the trifluoromethane sulfonic acid catalyst into the monomer/diol reaction mixture in a manner which avoids localized concentrations of the catalyst;
   d. allowing the polymerization reaction to proceed to completion;
   e. washing the reaction mixture with an aqueous basic peroxide solution; and
   f. isolating the product dihydroxy-terminated poly(2,2,3,3,4,4-hexafluoropentane-1,5-diol formal).

2. The process of claim 1 wherein $$0.0050 \leq (n_{acid} \times A)/n_{monomer} \leq 0.0350$$

3. The process of claim 2 wherein $$0.0075 \leq (n_{acid} \times A)/n_{monomer} \leq 0.0250$$

4. The process of claim 3 wherein $$0.0100 \leq (n_{acid} \times A)/n_{monomer} \leq 0.0150$$

5. The process of claim 1 wherein the reaction is run at a temperature in the range of from 50° C. to 70° C.

6. The process of claim 5 wherein the reaction is run at a temperature of from 55° C. to 65° C.

7. The process of claim 5 wherein the reaction is run at a temperature of about 60° C.

* * * * *